United States Patent

Lachhein et al.

Patent Number: 5,157,121
Date of Patent: Oct. 20, 1992

[54] PROCESS FOR THE PREPARATION OF N-ALKYLSULFONYLAMINOSULFONYLUREAS

[75] Inventors: Stephen Lachhein, Hofheim am Taunus; Lothar Willms, Hillscheid, both of Fed. Rep. of Germany

[73] Assignee: Hoechst Aktiengesellschaft, Frankfurt am Main, Fed. Rep. of Germany

[21] Appl. No.: 731,460

[22] Filed: Jul. 17, 1991

[30] Foreign Application Priority Data

Jul. 19, 1990 [DE] Fed. Rep. of Germany ....... 4022983

[51] Int. Cl.$^5$ ................ C07D 239/50; C07D 239/42; C07D 239/48
[52] U.S. Cl. .................... 544/320; 544/321; 544/323; 544/332
[58] Field of Search ............... 544/320, 321, 323, 332

[56] References Cited

U.S. PATENT DOCUMENTS 4,534,790  8/1985  Wolf ..................................... 544/212
4,601,747  7/1986  Willms et al. ......................... 71/92

FOREIGN PATENT DOCUMENTS 0131258  8/1989  European Pat. Off. .

OTHER PUBLICATIONS

J. March, (3rd ed.) p. 444 (1985).
Paquin, Angew Chem. 60, pp. 316-320 (1948).
Preiss, Chem. Ber. 111, pp. 1915-1921 (1978).
Arya, Indian J. Chem. Sec., B21, pp. 941, 943-944 (1982).

Primary Examiner—John M. Ford
Attorney, Agent, or Firm—Curtis, Morris & Safford

[57] ABSTRACT

Known herbicides of the formula (I)

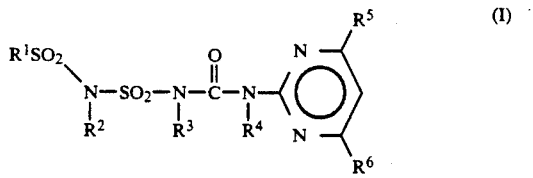

in which
 $R^1$ is alkyl, alkenyl or alkynyl, which are optionally substituted by halogen, alkoxy or alkoxycarbonyl,
 $R^2$ is H, alkyl, alkenyl, alkynyl or cycloalkyl,
 $R^3$ and $R^4$ are H or alkyl,
 $R^5$ and $R^6$ are H, alkyl or alkoxy, each of which can be substituted by halogen, alkoxy or alkylthio, or are halogen, alkylthio, alkylamino or dialkylamino, or, if $R^2$ or $R^3$ is H, their salts with bases, can be obtained when compounds of the formula II $$R^1-SO_2-NR^2-SO_2-NR^3-CO-OR^7 \qquad (II)$$

in which
 $R^1$, $R^2$ and $R^3$ are as defined above,
are reacted with compounds of the formula III

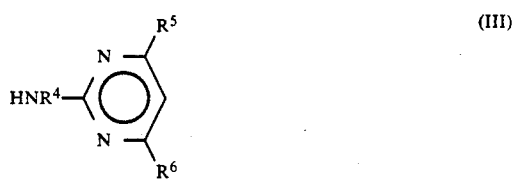

in which
 $R^4$, $R^5$ and $R^6$ are as defined above and
 $R^7$ is alkyl, haloalkyl or optionally substituted phenyl,
in an inert organic solvent, to give the compounds of the formula I.

21 Claims, No Drawings

PROCESS FOR THE PREPARATION OF N-ALKYLSULFONYLAMINOSULFONYLUREAS

The present invention relates to a process for the preparation of the compounds of the formula I

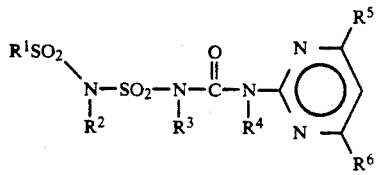   (I)

in which
- $R^1$ is $(C_1-C_6)$-alkyl, $(C_2-C_6)$-alkenyl or $(C_2-C_6)$-alkynyl, each of the 3 radicals mentioned being unsubstituted or mono- or polysubstituted by radicals from the group comprising halogen, $(C_1-C_4)$-alkoxy and $[(C_1-C_4)$-alkoxy]carbonyl,
- $R^2$ is hydrogen, $(C_1-C_6)$-alkyl, $(C_2-C_6)$-alkenyl, $(C_2-C_6)$-alkynyl or $(C_3-C_6)$-cycloalkyl,
- $R^3$ and $R^4$ independently of one another are hydrogen or $(C_1-C_4)$-alkyl,
- $R^5$ and $R^6$ independently of one another are hydrogen, $(C_1-C_4)$-alkyl or $(C_1-C_4)$-alkoxy, the 2 last-mentioned radicals being unsubstituted or mono- or polysubstituted by radicals from the group comprising halogen, alkoxy and alkylthio, or are halogen, $(C_1-C_4)$-alkylthio, $(C_1-C_4)$-alkylamino or $(C_1-C_4)$-dialkylamino, and, if $R^2$ and $R^3$ are hydrogen, their physiologically acceptable salts with bases.

Compounds of the formula I are known and are employed as plant protection agents having a herbicidal action; see, for example, EP-A- 0,131,258.

This publication also already refers to, or describes, a range of processes by which compounds of the formula I can be prepared.

The disadvantage of the known processes is the relatively low yields of not more than 65–70%. As a consequence of these low yields, considerable amounts of contamination and by-products are produced. From an ecological as well as an economical point of view, these described processes cannot be carried out on a large scale, since the large amounts of by-products and waste which would result thereby are unacceptable, and their disposal, for example by incineration, is complicated. Moreover, such low yield means that the loss of starting materials employed is drastic.

A novel process has now been found by which the compounds of the formula I can be prepared in a surprisingly high yield and purity.

The process according to the invention is distinguished by the fact that compounds of the formula II

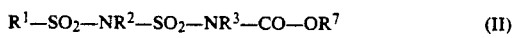

in which
$R^1$, $R^2$ and $R^3$ are as defined above and
$R^7$ is alkyl, haloalkyl or optionally substituted phenyl, are reacted with compounds of the formula III

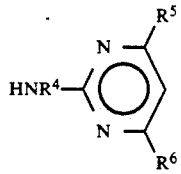   (III)

in which
$R^4$, $R^5$ and $R^6$ are as defined above,
in an inert organic solvent, to give the compounds of the formula I.

In the formulae mentioned and in the following text, alkyl, alkoxy, haloalkyl, alkylamino and alkylthio radicals as well as the corresponding unsaturated and/or substituted radicals can, unless otherwise indicated, in each case be straight-chain or branched as far as the carbon chain is concerned; alkyl radicals, also in the compound meanings such as alkoxy, haloalkyl, etc., are, for example, methyl, ethyl, n- or i-propyl, n-, i-, t- or 2-butyl; alkenyl and alkynyl radicals have the meaning of the possible unsaturated radicals which correspond to the alkyl radicals, such as 2-propenyl, 2- or 3-butenyl, 2-propynyl, 2- or 3-butynyl; optionally substituted phenyl is, for example, phenyl which is unsubstituted or substituted by one or more, preferably 1 to 3, radicals from the group comprising halogen, $(C_1-C_4)$-alkyl, $(C_1-C_4)$-alkoxy, $(C_1-C_4)$-haloalkyl, $(C_1-C_4)$-thioalkyl, $(C_1-C_4$-alkoxy)carbonyl, $(C_1-C_4$-alkyl)sulfonyl, cyano and nitro; halogen, also halo in haloalkyl etc., is fluorine, chlorine, bromine or iodine, preferably fluorine, chlorine or bromine.

Preferred processes amongst the processes according to the invention for the preparation of the compounds of the formula I are those in which $R^1$ and $R^2$ independently of one another are $(C_1-C_3)$-alkyl or $(C_1-C_3)$-alkenyl, in particular $(C_1-C_2)$-alkyl, $R^3$ and $R^4$ are hydrogen, $R^5$ and $R^6$ independently of one another are $(C_1-C_2)$-alkyl or $(C_1-C_2)$-alkoxy, in particular methyl or methoxy.

$R^7$ is preferably $(C_1-C_4)$-alkyl, $(C_1-C_4)$-haloalkyl or phenyl, in particular ethyl or phenyl.

As a rule, the yields in the process according to the invention are at least 95% of theory, and the purities of the sulfonylureas I formed are usually higher than 98% by weight.

The process according to the invention is carried out in inert organic solvents. Examples of types of solvents in this context are aromatic, optionally halogenated hydrocarbons and aprotic polar solvents such as dialkylalkanoylamides, dialkyl sulfoxides, polyalkylene glycol dialkyl ethers, N-alkylated cyclic amides and nitriles. Examples of preferred solvents are toluene, xylene, chlorobenzene, dimethylformamide, dimethyl sulfoxide, di-, tri- or tetraethylene glycol dialkyl ethers, in particular di-, tri- or tetraethylene glycol dimethyl ether or di-, tri- or tetraethylene glycol diethyl ether, N-methylpyrrolidone, acetonitrile, and also mixtures of two or more of the solvents mentioned.

As a rule, the ratio of the compound of the formula II to the compound of the formula III is equimolar or the former is employed in a slight excess. A preferred molar ratio of II:III is from 1:1 to 1.2:1, in particular 1:1 to 1.1:1.

It is an advantage of the process according to the invention that the solvents can be recycled in virtually quantitative yield since the products of the formula I precipitate from the reaction medium in the form of sparingly soluble compounds in high purity and yield. The solvents can subsequently be purified, for example by distillation, and then fed back into the production process.

The reaction temperatures range preferably from 0° C. up to the boiling point of the solvent employed, in particular from room temperature (for example 20° C.) to 110° C.

The starting compounds of the formulae II and III which are required for the preparation of the compounds according to the invention of the general formula I can be prepared by processes known from the literature.

For example, the compounds of the formula II are obtained analogously to customary methods (see, for example, Tietze und Eicher in "Reaktionen und Synthesen" [Reactions and Syntheses], p. 92, Thieme Verlag, Stuttgart 1981), by reacting the corresponding sulfonamides IV with chloroformic esters V,

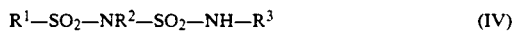

$$R^1-SO_2-NR^2-SO_2-NH-R^3 \quad (IV)$$

$$Cl-CO-OR^7 \quad (V)$$

which, in turn, are accessible in very high yield by customary laboratory methods (see, for example, "Organikum", 7th edition, p. 539, VEB Deutscher Verlag der Wissenschaften, Berlin 1967) by reacting the corresponding sulfonamides VI with the corresponding sulfamoylchlorides VII

$$R^1-SO_2-NH-R^2 \quad (VI)$$

$$Cl-SO_2-NH-R^3 \quad (VII)$$

The heterocycles of the formula III are either commercially available or can be prepared easily by suitable laboratory methods; see, for example, U.S. Pat. No. 4,310,470; EP 0,024,200; U.S. Pat. No. 4,299,960; M. J. Langerman, C. K. Banks, JACS 73, 3011 (1951).

The process according to the invention must be regarded as particularly surprising because the starting material of the formula II contains a plurality of activated electrophilic and nucleophilic centers, where in particular the electrophilic centers could all react in principle with the nucleophilic substances of the formula III and could therefore give a large number of by-products because of fragmentation reactions; cf. Beyer, Lehrbuch der org. Chemie [Textbook of Organic Chemistry], 19th edition, p. 128, Hirzel Verlag Stuttgart), according to which sulfonyl groups are very good leaving groups.

However, the secondary reactions mentioned surprisingly are virtually nonexistent in the process according to the invention, because the process according to the invention usually gives yields of more than 95% of theory and purities of more than 98%.

The process according to the invention therefore represents a process for synthesizing the compounds of the formula I in virtually quantitative yields which is novel and simple, and is easily reproducible and highly selective, even on a larger, industrial scale.

The process can be carried out batchwise or continuously.

In the following test, the process according to the invention will be illustrated with the aid of a number of examples. Unless otherwise specified, percentages are by weight.

EXAMPLE 1

1-[(N-Methylsulfonyl-N-methylamino)sulfonyl]-3-(4,6-dimethoxy-2-pyrimidyl)urea 52.0 g of ethyl (N-methylsulfonyl-N-methylamino)-sulfonylcarbamate are dissolved in 500 ml of chlorobenzene, 31.0 g of 2-amino-4,6-dimethoxypyrimidine are added at room temperature with stirring, and the mixture is heated at 80° C. for 3 hours. After cooling to 0° C., the precipitate is filtered off and washed with 100 ml of chlorobenzene. 72.7 g of the desired product of a purity of 98.5% are obtained, which corresponds to a yield of 97.2% of theory. The melting point of the product is 185°–186° C.

EXAMPLE 2

1-[(N-Methylsulfonyl-N-methylamino)sulfonyl]-3-(4-methoxy-6-methyl-2-pyrimidyl)urea 52.0 g of ethyl (N-methylsulfonyl-N-methylamino)-sulfonylcarbamate are dissolved in 500 ml of chlorobenzene, 27.8 g of 2-amino-4-methoxy-6-methylpyrimidine are added at room temperature, and the mixture is heated at 50° C. for 5 hours. After cooling to 0° C., the precipitate is filtered off. After washing with 100 ml of chlorobenzene, 68.8 g of the desired product of a purity of 98.9% are obtained; this corresponds to a yield of 96.4% of theory. The melting point of the product is 118°–120° C.

EXAMPLE 3

1-[(N-Ethylsulfonyl-N-ethylamino)sulfonyl]-3-(4,6-diethoxy-2-pyrimidyl)urea 65.2 g of phenyl (N-ethylsulfonyl-N-methylamino)-sulfonylcarbamate are dissolved in 700 ml of toluene, 36.6 g of 2-amino-4,6-diethoxypyrimidine are added at room temperature, and the mixture is heated at 110° C. for 2 hours. After cooling to room temperature, the precipitate is filtered at 0° C. and washed with 200 ml of toluene. 82.6 g of the desired product of a purity of 98.1% are obtained, which corresponds to a yield of 95.3% of theory.

The melting point of the product is 174°–176° C.

The compounds of the formula I which are listed in Table 1 below can be synthesized analogously to Examples 1 to 3.

TABLE 1

| Ex. No. | $R^1$ | $R^2$ | $R^3$ | $R^4$ | $R^5$ | $R^6$ | M.p. (°C.) |
|---|---|---|---|---|---|---|---|
| 4 | $CH_3$ | $CH_3$ | H | H | $CH_3$ | $CH_3$ | 150–151 |
| 5 | $CH_3$ | $C_3H_7$ | H | H | $CH_3$ | $CH_3$ | 149–151 |
| 6 | $CH_3$ | $C_3H_7$ | H | H | $OCH_3$ | $CH_3$ | 141–143 |
| 7 | $CH_3$ | $CH_2=CHCH_2$ | H | H | $CH_3$ | $CH_3$ | 139–141 |
| 8 | $CH_3$ | $CH_2=CHCH_2$ | H | H | $OCH_3$ | $CH_3$ | 159–161 |
| 9 | $CH_2Cl$ | $CH_3$ | H | H | $CH_3$ | $CH_3$ | 146–148 |
| 10 | $CH_3$ | $C_3H_7$ | H | H | $OCH_3$ | $OCH_3$ | 156–157 |
| 11 | $CH_3$ | $CH(CH_3)_2$ | H | H | $OCH_3$ | $OCH_3$ | 121–123 |

TABLE 1-continued

| Ex. No. | $R^1$ | $R^2$ | $R^3$ | $R^4$ | $R^5$ | $R^6$ | M.p. (°C.) |
|---|---|---|---|---|---|---|---|
| 12 | $CH_3$ | $CH(CH_3)_2$ | H | H | Cl | $OCH_3$ | 153-155 |
| 13 | $C_2H_5$ | $C_2H_5$ | H | H | $OCH_3$ | $OCH_3$ | |
| 14 | $CH_3$ | $CH_3$ | H | H | $OCH_3$ | $OC_2H_5$ | |
| 15 | $CH_3$ | $CH_3$ | H | $CH_3$ | $OCH_3$ | $OCH_3$ | |
| 16 | $CH_3$ | $C_2H_5$ | $CH_3$ | $CH_3$ | $C_2H_5$ | $OCH_3$ | |
| 17 | $C_3H_7$ | $CH_3$ | H | H | $CH_3$ | $CH_3$ | |
| 18 | $C_4H_9$ | $CH_3$ | H | H | $OCH_3$ | $OCH_3$ | |
| 19 | $CH_3$ | cyclo-$C_6H_{11}$ | H | H | $OCH_3$ | $OCH_3$ | |
| 20 | $CH_3$ | $CH_2-C\equiv CH$ | $CH_3$ | H | $CH_3$ | $OCF_2H$ | |
| 21 | $CH_3$ | $CH_2-CO_2CH_3$ | H | H | $CH_3$ | $CH_3$ | |

We claim:
1. A process for the preparation of the compounds of the formula I

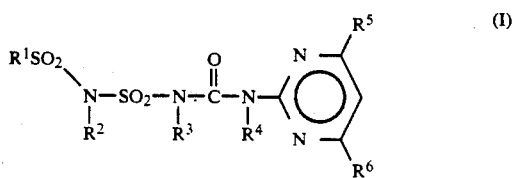

in which
$R^1$ is $(C_1-C_6)$-alkyl, $(C_2-C_6)$-alkenyl or $(C_2-C_6)$-alkynyl, each of the 3 radicals mentioned being unsubstituted or mono- or polysubstituted by halogen, $(C_1-C_4)$-alkoxy and $[(C_1-C_4)$-alkoxy]carbonyl,
$R^2$ is hydrogen, $(C_1-C_6)$-alkyl, $(C_2-C_6)$-alkenyl, $(C_2-C_6)$-alkynyl or $(C_3-C_6)$-cycloalkyl,
$R^3$ and $R^4$ independently of one another are hydrogen or $(C_1-C_4)$-alkyl,
$R^5$ and $R^6$ independently of one another are hydrogen, $(C_1-C_4)$-alkyl or $(C_1-C_4)$-alkoxy, the 2 last-mentioned radicals being unsubstituted or mono- or polysubstituted by radicals from the group comprising halogen, alkoxy and alkylthio, or are halogen, $(C_1-C_4)$-alkylthio, $(C_1-C_4)$-alkylamino or $(C_1-C_4)$-dialkylamino,
and, if $R^2$ and $R^3$ are hydrogen, their physiologically acceptable salts with bases, which comprises reacting compounds of the formula II

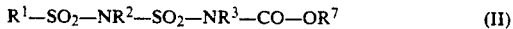

$$R^1-SO_2-NR^2-SO_2-NR^3-CO-OR^7 \quad (II)$$

in which
$R^1$, $R^2$ and $R^3$ are as defined above and $R_7$, with compounds of the formula III
$R^7$ is alkyl, haloalkyl or optionally substituted phenyl,

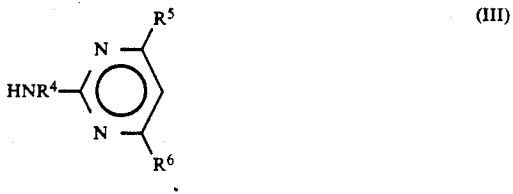

in which
$R^4$, $R^5$ and $R^6$ are as defined above
in an inert organic solvent, to give the compounds of the formula I.
2. The process as claimed in claim 1, in which $R^1$ and $R^2$ independently of one another are $(C_1-C_3)$-alkyl or $(C_1-C_3)$-alkenyl, $R^3$ and $R^4$ are hydrogen, and $R^5$ and $R^6$ independently of one another are $(C_1-C_2)$-alkyl or $(C_1-C_2)$-alkoxy.
3. The process as claimed in claim 1, in which $R^1$ is $(C_1-C_2)$-alkyl, $R^2$ is $(C_1-C_3)$-alkyl or $(C_1-C_3)$-alkenyl, $R^3$ and $R^4$ are hydrogen, $R^5$ is methyl or methoxy and $R^6$ is methyl or methoxy.
4. The process as claimed in claim 1, in which $R^7$ is $(C_1-C_4)$-alkyl, $(C_1-C_4)$-haloalkyl or phenyl.
5. The process as claimed in claim 1, wherein the inert organic solvents employed are aromatic hydrocarbons, halogenated aromatic hydrocarbons or aprotic polar solvents, or mixtures of the solvents mentioned.
6. The process as claimed in claim 1, wherein the temperatures at which the reaction is carried out are ranging from 0° C. to the boiling point of the solvent employed.
7. The process as claimed in claim 6, wherein the reaction temperature ranges from room temperature up to 110° C.
8. The process as claimed in claim 1, wherein the compounds II and III are reacted in a molar ratio of 1:1 to 1.2:1.
9. The process as claimed in claim 8, wherein the molar ratio is 1:1 to 1.1:1.
10. The process as claimed in claim 1, wherein the process is carried out batchwise or continuously.
11. The process as claimed in claim 5, wherein the compounds II and III are reacted in a molar ratio of 1:1 to 1.2:1 at a temperature of from 0° C. to the boiling point of the organic solvent.
12. The process as claimed in claim 11, wherein the temperature is from room temperature to 110° C.
13. The process as claimed in claim 12, wherein the compounds II and III are reacted in a molar ratio of 1:1 to 1.1:1.
14. The process as claimed in claim 1, wherein $R^1$ is methyl or ethyl, $R^2$ is methyl or ethyl, $R^3$ is hydrogen, $R^4$ is hydrogen, $R^5$ is methyl, ethyl, methoxy or ethoxy, $R^6$ is methyl, ethyl, methoxy or ethoxy and $R^7$ is ethyl or phenyl.
15. The process as claimed in claim 14, wherein $R^1$ is methyl, $R^2$ is methyl, $R^5$ is methoxy, $R^6$ is methoxy and $R^7$ is ethyl.
16. The process as claimed in claim 14, wherein $R^1$ is methyl, $R^2$ is methyl, $R^5$ is methoxy, $R^6$ is methyl and $R^7$ is ethyl.
17. The process as claimed in claim 14, wherein $R^1$ is methyl, $R^2$ is methyl or ethyl, $R^5$ is methoxy, $R^6$ is methoxy and $R^7$ is phenyl.
18. The process as claimed in claim 14, wherein $R^1$ is methyl, $R^2$ is methyl or ethyl, $R^5$ is methoxy, $R^6$ is methyl and $R^7$ is phenyl.

19. The process as claimed in claim 14, wherein $R^1$ is ethyl, $R^2$ is methyl or ethyl, $R^5$ is ethoxy, $R^6$ is ethoxy and $R^7$ is phenyl.

20. The process as claimed in claim 14, wherein the solvent is selected from the group consisting of aromatic hydrocarbons and halogenated hydrocarbons; the reaction temperature is from 20° C. to 110° C.; and compounds II and III are reacted in a molar ratio of 1:1 to 1.2:1.

21. The process as claimed in claim 14, wherein the solvent is selected from the group consisting of chlorobenzene and toluene; and compounds II and III are reacted in a molar ratio of 1:1 to 1.1:1.

* * * * *